(12) United States Patent
Guo et al.

(10) Patent No.: US 10,093,644 B2
(45) Date of Patent: Oct. 9, 2018

(54) 3-[(BENZO[D][1,3]DIOXOLAN-4-YL)-OXY]-3-ARYLPROPYLAMINE TYPE COMPOUNDS AND APPLICATIONS THEREOF

(71) Applicant: NHWA PHARMA. CORPORATION, Xuzhou, Jiangsu (CN)

(72) Inventors: Qiang Guo, Xuzhou (CN); Song Zhao, Xuzhou (CN); Zhiqiang Liu, Xuzhou (CN); Xiangqing Xu, Xuzhou (CN); Guisen Zhang, Xuzhou (CN)

(73) Assignee: NHWA PHARMA. CORPORATION, Xuzhou, Jiangsu (CN)

( * ) Notice: Subject to any disclaimer, the term of this patent is extended or adjusted under 35 U.S.C. 154(b) by 0 days.

(21) Appl. No.: 15/539,199

(22) PCT Filed: Dec. 24, 2015

(86) PCT No.: PCT/CN2015/098641
§ 371 (c)(1),
(2) Date: Jun. 23, 2017

(87) PCT Pub. No.: WO2016/101898
PCT Pub. Date: Jun. 30, 2016

(65) Prior Publication Data
US 2017/0369466 A1 Dec. 28, 2017

(30) Foreign Application Priority Data

Dec. 25, 2014 (CN) .......................... 2014 1 0820494

(51) Int. Cl.
| C07D 317/64 | (2006.01) |
| A61P 25/24 | (2006.01) |
| C07D 319/08 | (2006.01) |
| A61K 31/343 | (2006.01) |
| A61K 9/20 | (2006.01) |
| A61K 9/48 | (2006.01) |
| A61K 31/36 | (2006.01) |

(52) U.S. Cl.
CPC ............. *C07D 317/64* (2013.01); *A61K 9/20* (2013.01); *A61K 9/48* (2013.01); *A61K 31/343* (2013.01); *A61K 31/36* (2013.01); *C07D 319/08* (2013.01)

(58) Field of Classification Search
CPC ... C07D 319/08; C07D 317/64; A61K 31/343
See application file for complete search history.

(56) References Cited

U.S. PATENT DOCUMENTS 4,018,895 A  4/1977 Molloy et al.

FOREIGN PATENT DOCUMENTS

| CN | 1019113 B | 11/1992 |
| CN | 101613347 A | 12/2009 |

OTHER PUBLICATIONS

"International Application No. PCT/CN2015/098641, International Search Report dated Mar. 24, 2016", w/ English Translation, (dated Mar. 24, 2016), 5 pgs.
"International Application No. PCT/CN2015/098641, Written Opinion dated Mar. 24, 2016", (dated Mar. 24, 2016), 4 pgs.
Berge, Stephen M, et al., "Pharmaceutical Salts", Journal of Pharmaceutical Sciences, 66(1), (Jan. 1977), 1-19.

*Primary Examiner* — Susanna Moore
(74) *Attorney, Agent, or Firm* — Schwegman Lundberg & Woessner, P.A.

(57) ABSTRACT

The present invention relates to 3-[(benzo[d][1,3]dioxolan-4-yl)-oxy]-3-arylpropylamine compounds of formula I or pharmaceutically acceptable salts thereof and use thereof. The compound may be used to prepare an antidepressant agent.

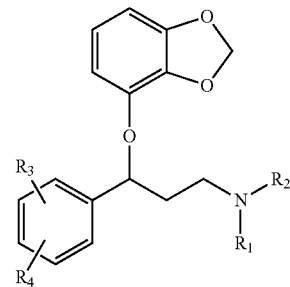

10 Claims, No Drawings

3-[(BENZO[D][1,3]DIOXOLAN-4-YL)-OXY]-3-ARYLPROPYLAMINE TYPE COMPOUNDS AND APPLICATIONS THEREOF

PRIORITY APPLICATIONS

This application is a U.S. National Stage Filing under 35 U.S.C. 371 from International Application No. PCT/CN2015/098641, filed on 24 Dec. 2015, and published as WO2016/101898 on 30 Jun. 2016, which claims the benefit of priority to Chinese Application No. 201410820494.8, filed on 25 Dec. 2014; which applications and publication are incorporated herein by reference in their entirety.

TECHNICAL FIELD

The invention belongs to the field of medicinal chemistry and particularly relates to a 3-[(benzo[d][1,3]dioxolan-4-yl)-oxy]-3-arylpropylamine compound and applications thereof.

BACKGROUND

Depression is the most common psychiatric disease against human health. By far 3-5% of the population of the world suffers from depression. It is expected by 2020 depression might be the major disease second to heart disease.

Medicines are commonly used to treat depression and comprise tricyclic antidepressant agent like imipramine etc.; monoamine oxidase inhibitor like moclobemide etc.; selective 5-HT reuptake inhibitor like fluoxetine etc.; selective NE reuptake inhibitor like reboxetine etc.; 5-HT and NE double reuptake inhibitor like duloxetine etc.

Although various antidepressant agents have been clinically used, some medicines have the disadvantages of low response rate, long onset time and potential adverse effect and thus a large number of patients are ineffective to various therapies and some of them even turn to electrofit therapy. Accordingly, it is desirable to develop novel antidepressant agent.

U.S. Pat. No. 4,018,895 discloses antidepressant agents including fluoxetine having the following structure:

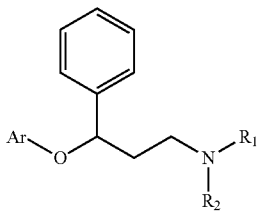

wherein, Ar is naphthalene ring or substituted benzene ring, R1 and R2 are each H or methyl.

CN 1019113 discloses antidepressant agents including duloxetine having the following structure:

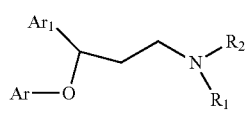

wherein, Ar is naphthalene ring or substituted benzene ring; Ar1 is cycloalkyl, furyl, thienyl or thiazolyl; R1 and R2 are each H or CH$_3$.

CN 101613347 discloses antidepressant compounds including ammuxetine having the following structure:

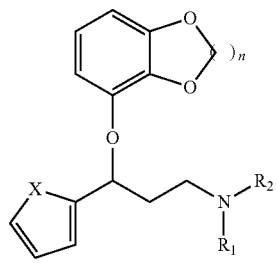

wherein X is O or S, R1 and R2 each independently represent H or C1-C3 alkyl.

Although the above medicines like duloxetine and ammuxetine have relatively good activity against depression, their structures are not stable against acid, are prone to decomposition in stomach, not suitable for disintegration and uptake in stomach and thus are not suitable for preparing normal tablet and have high selectivity for formulation.

SUMMARY

In first aspect, provided is a 3-[(benzo[d][1,3]dioxolan-4-yl)-oxy]-3-arylpropylamine compound, an optical isomer thereof or a pharmaceutically acceptable salt thereof. Specifically, provided is a compound of formula I, an optical isomer thereof or a pharmaceutically acceptable salt thereof:

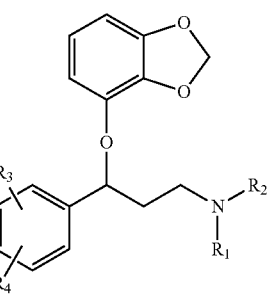

I wherein,
$R_1$ and $R_2$ are independently hydrogen or $C_{1-5}$ alkyl; and
$R_3$ and $R_4$ are independently hydrogen, halogen, substituted or unsubstituted $C_{1-5}$ alkyl or $C_{1-3}$ alkoxyl.

In a preferable embodiment, the halogen is fluorine (F), chlorine (Cl), bromine (Br) or iodine (I).

In a preferable embodiment, the unsubstituted $C_{1-5}$ alkyl is methyl, ethyl or isopropyl.

In a preferable embodiment, the substituted $C_{1-5}$ alkyl is trifluoromethyl.

In a preferable embodiment, the $C_{1-3}$ alkoxyl is methoxyl or ethoxyl.

Preferably, the compound according to the invention or the pharmaceutically acceptable salt thereof (i.e. the compound of formula I or the pharmaceutically acceptable salt thereof) is selected from any one of the following compounds or the pharmaceutically acceptable salts thereof:

3-[(benzo[d][1,3]dioxolan-4-yl)-oxy]-N,N-dimethyl-3-phenylpropylamine

3-[(benzo[d][1,3]dioxolan-4-yl)-oxy]-N-methyl-3-phenylpropylamine

3-[(benzo[d][1,3]dioxolan-4-yl)-oxy]-3-(4-fluorophenyl)-N,N-dimethylpropylamine

3-[(benzo[d][1,3]dioxolan-4-yl)-oxy]-3-(4-fluorophenyl)-N-methylpropylamine

3-[(benzo[d][1,3]dioxolan-4-yl)-oxy]-3-(4-chlorophenyl)-N,N-dimethylpropylamine

3-[(benzo[d][1,3]dioxolan-4-yl)-oxy]-3-(4-chlorophenyl)-N-methylpropylamine

3-[(benzo[d][1,3]dioxolan-4-yl)-oxy]-3-(3-chlorophenyl)-N,N-dimethylpropylamine

3-[(benzo[d][1,3]dioxolan-4-yl)-oxy]-3-(3-chlorophenyl)-N-methylpropylamine

3-[(benzo[d][1,3]dioxolan-4-yl)-oxy]-3-(3-fluorophenyl)-N,N-dimethylpropylamine

3-[(benzo[d][1,3]dioxolan-4-yl)-oxy]-3-(3-fluorophenyl)-N-methylpropylamine

3-[(benzo[d][1,3]dioxolan-4-yl)-oxy]-3-(3-methoxylphenyl)-N,N-dimethylpropylamine 3-[(benzo[d][1,3]dioxolan-4-yl)-oxy]-3-(3-methoxylphenyl)-N-methylpropylamine 3-[(benzo[d][1,3]dioxolan-4-yl)-oxy]-3-(3-methylphenyl)-N,N-dimethylpropylamine 3-[(benzo[d][1,3]dioxolan-4-yl)-oxy]-3-(3-methylphenyl)-N-methylpropylamine 3-[(benzo[d][1,3]dioxolan-4-yl)-oxy]-3-(2-fluorophenyl)-N,N-dimethylpropylamine 3-[(benzo[d][1,3]dioxolan-4-yl)-oxy]-3-(2-fluorophenyl)-N-methylpropylamine 3-[(benzo[d][1,3]dioxolan-4-yl)-oxy]-3-(3,4-dichlorophenyl)-N,N-dimethylpropylamine 3-[(benzo[d][1,3]dioxolan-4-yl)-oxy]-3-(3,4-dichlorophenyl)-N-methylpropylamine.

In second aspect, provided is a pharmaceutical composition, comprising a compound of formula I and/or a pharmaceutically acceptable salt thereof in a therapeutically effective amount and pharmaceutically acceptable carrier and/or excipient.

In third aspect, provided is a compound of formula I or a pharmaceutically acceptable salt thereof or a pharmaceutical composition according to the invention for use in preventing or treating neuropsychiatric disease. In a preferable embodiment, the neuropsychiatric disease is depression.

Provided is also use of a compound of formula I or a pharmaceutically acceptable salt thereof or a pharmaceutical composition according to the invention for the manufacture of a medicament for preventing or treating neuropsychiatric disease. In a preferable embodiment, the neuropsychiatric disease is depression.

Provided is also a method for preventing or treating neuropsychiatric disease, comprising administrating a subject in need thereof a compound of formula I or a pharmaceutically acceptable salt thereof or a pharmaceutical composition according to the invention. In a preferable embodiment, the neuropsychiatric disease is depression.

DETAILED DESCRIPTION

Definition

The chemical terms used herein have common meaning in the art. Unless specifically defined otherwise, proportion and percentage are calculated based on weight herein.

The term "$C_{1-5}$ alkyl" used herein refers to a linear or branched saturated alkyl having 1-5 carbon atoms (including 1, 2, 3, 4 or 5), preferably 1-4 carbon atoms (i.e. $C_{1-4}$ alkyl), more preferably 1-3 carbon atoms (i.e. $C_{1-3}$ alkyl) or 1-2 carbon atoms (i.e. $C_{1-2}$ alkyl). The examples comprise but not limited to methyl, ethyl, n-propyl, isopropyl, n-butyl, isobutyl, sec-butyl, t-butyl, pentyl or the like, preferably methyl, ethyl and isopropyl.

The term "$C_{1-3}$alkoxyl" used herein refers to "$C_{1-3}$ alkyl-O—", which links to the other part of the molecule via an oxygen atom, wherein "$C_{1-3}$ alkyl" is defined as above. The examples comprises but not limited to methoxyl, ethoxyl, propoxyl, isopropoxyl or the like, preferably, methoxyl and ethoxyl.

The term "halogen" refers to F, Cl, Br or I.

The term "substituted" means that one or more hydrogen atoms (eg. 1, 2, 3, 4, 5, 6, 7, 8 or more) on a given atom are replaced by a selection from given groups, provided that the valence of the particular atom is normal and the compound after substitution is stable. The examples of substituent comprises but not limited to halogen (e.g. F, Cl, Br or I), OH, $NH_2$, =O, $NMe_2$, $CONH_2$, $CH_2NMe_2$, $NHSO_2Me$, COMe, OMe, SMe, COOMe, COOEt, $CH_2COOH$, $OCH_2COOH$, COOH, SOMe, $SO_2Me$, $SO_2NH_2$, $SO_2NHMe$, $SO_2CH_2CH_2OH$, $SF_5$, $SO_2NMe_2$, $OCF_3$, $SO_2CF_3$, COMe, CN, $CF_3$, $C_{1-3}$ alkoxyl, $C_{1-5}$ alkyl, $C_{3-10}$ cycloalkyl, $C_{6-10}$aryl or the like. For example, $C_{1-5}$ alkyl may be optionally substituted by one or more above substituents so as to form fluoromethyl, difluoromethyl, trifluoromethyl, dichloroethyl, trichloroethyl or the like. Similarly. $C_{1-3}$alkoxyl may be optionally substituted by one or more above substituents so as to form difluoromethoxyl, dichloroethoxyl or the like.

The term "optional" or "optionally" means the event described subsequent thereto may or may not happen. For example, when a group is optionally substituted, it may be unsubstituted or substituted by a given substituent in any suitable means.

Pharmaceutically Acceptable Salt

The term "pharmaceutically acceptable salt" used herein refers to relatively non-toxic inorganic or organic acid addition salt of the compound according to the invention. For example, please refer to S. M. Berge et al., "Pharmaceutical Salts," J. Pharm. Sci. 1977, 66, 1-19.

The pharmaceutically acceptable salts of the compound according to the invention comprise but not limited to those from the following group: oxalate, hydrochloride, hydrobromide, hydriodate, nitrate, sulfate, bisulfate, phosphate, acid phosphate, acetate, lactate, citrate, tartrate, maleate, fumarate, methanesulfonate, gluconate, saccharate, benzoate, ethanesulfonate, benzenesulfonate and p-toluenesulfonate; preferably oxalate.

Isomer

The compound according to the invention may contain asymmetric or chiral center(s) and thus may be present in various stereoisomers. Such forms may be individual stereoisomer or any mixture of the stereoisomers in any ratio. Unless stated otherwise, the invention is intended to encompass all of the stereoisomers and mixture thereof (including racemate mixture). Therefore, provided is an optical isomer of the compound of formula I or a pharmaceutically acceptable salt thereof. Preferably, the optical isomer is pharmaceutically acceptable. Purification and isolation of such isomers may be achieved through standard technology known in the art. For example, any suitable technology in the art, like chromatography, especially chiral chromatography, may be used to separate individual stereoisomer like individual enantiomer or diastereomer according to the invention.

Pharmaceutical Composition and Administration

The compound according to the invention or the pharmaceutically acceptable salt thereof may function systematically and/or locally. According to practical requirement, the compound according to the invention or the pharmaceutically acceptable salt thereof may be administered through suitable means, comprising but not limited to oral, injectable, parenteral, local, rectal, percutaneous administration or the like.

According to different administration routes, the compound according to the invention or the pharmaceutically acceptable salt thereof may be formulated into administration forms as required, comprising but not limited to tablet, powder, capsule, solution, suspension, suppository, patch, granule, ointment, lotion or the like. This could be achieved through a means in the art. For example, the compound according to the invention or the pharmaceutically acceptable salt thereof may be mixed with pharmaceutically acceptable adjuvant. Examples of the pharmaceutically acceptable adjuvant used in the invention comprise but not limited to solvent, emulsifier, dispersant, wetting agent, binder, stabilizing agent, colorant and odour and/or taste masking agent.

The compound according to the invention or the pharmaceutically acceptable salt thereof may be used in combination with other agents known for treating neuropsychiatric disease. The agents known in the art for treating neuropsychiatric disease comprise for example, risperidone, aripiprazole, amisulpride, fluoxetine, alprazolam, midazolam, citalopram, diazepam or the like.

Accordingly, provided is a pharmaceutical composition, comprising the compound according to the invention and/or the pharmaceutically acceptable salt thereof in a therapeutically effective amount, and pharmaceutically acceptable adjuvant, optionally in combination with other agent(s) known for treating neuropsychiatric disease.

In an embodiment, the pharmaceutical composition according to the invention comprises the compound according to the invention and/or the pharmaceutically acceptable salt thereof in a therapeutically effective amount and pharmaceutically acceptable carrier and/or excipient.

The unit dosage of the pharmaceutical composition according to the invention may comprise 0.01-1000 mg, preferably 1.0-300 mg, more preferably 10-150 mg, most preferably 100 mg of the compound according to the invention and/or the pharmaceutically acceptable salt thereof. Alternatively, based on the total weight of the pharmaceutical composition, the pharmaceutical composition according to the invention may comprise at least 0.5 wt %, preferably 4 wt %-70 wt %, more preferably 10 wt %-50 wt %, most preferably 30 wt % of the compound according to the invention and/or the pharmaceutically acceptable salt thereof.

Dosage of the compound according to the invention or the pharmaceutically acceptable salt thereof contained in the present pharmaceutical composition depends on the type and severity of the disease or disorder and characteristic of the subject, for example general health, age, gender, weight and medicine tolerance. A person skilled in the art could determine appropriate dosage of the active compound of the invention according to these or other factors. Generally, the effective dosage of the medicine for central nervous system is well known to a person skilled in the art and the total daily dosage is generally about 0.05 mg-about 2000 mg.

Medical Use and Treating Method

Provided is a compound of formula I or a pharmaceutically acceptable salt thereof or a pharmaceutical composition according to the invention for use in preventing or treating neuropsychiatric disease.

Provided is also use of a compound of formula I or a pharmaceutically acceptable salt thereof or a pharmaceutical composition according to the invention for the manufacture of a medicament for preventing or treating neuropsychiatric disease.

Provided is further a method for preventing or treating neuropsychiatric disease, comprising administrating a subject in need thereof a compound of formula I and/or a pharmaceutically acceptable salt thereof or a pharmaceutical composition according to the invention.

In a preferable embodiment, the neuropsychiatric disease is depression.

The term "treating" or "treatment" used herein comprises overcoming, relieving, reducing, ameliorating or improving the disease or disorder. According, "treating" a subject with disease or disorder could mean partial or complete ameliorating of the symptoms of the subject, or unchange after treatment. The term "preventing" or "prevention" used in herein means lowering the risk of developing the disease or disorder. In some cases, the term "treating" encompasses "preventing".

The term "subject" used herein comprises mammal, preferably human.

Synthesis Process

The compound according to the invention may be synthesized according to the following procedures.

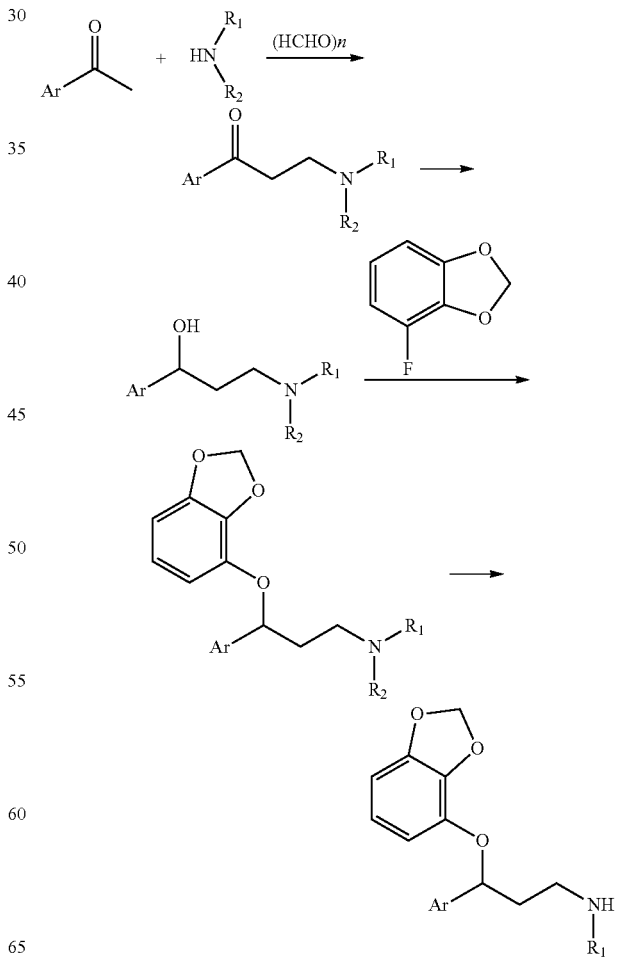

Specifically, the (substituted) acetophenone and dialkylamine hydrochloride and paraformaldehyde are dissolved in isopropanol, to which is added catalytic amount of hydrochloric acid and the reaction mixture is refluxed for 6-8 h to give 3-dialkyl amino-aryl-1-acetone, which is then reacted with sodium borohydride to obtain its hydroxide. The hydroxide is reacted with 4-fluorobenzo[1,3]dioxolane to give the target 3-[(benzo[d][1,3]dioxolan-4-yl)-oxy]-3-arylpropylamine with N atom substituted with di-alkyl groups. The target substituted with di-alkyl groups is removed an alkyl group under the action of phenyl chloroformate to obtain the target 3-[(benzo[d][1,3]dioxolan-4-yl)-oxy]-3-arylpropylamine with N atom substituted with mono-alkyl group.

Beneficial Effect

The compound according the invention has similar antidepressant activity as duloxetine and ammuxetine but higher therapeutic index, showing a higher safety. Moreover, according the gastric acid simulated experiment, the compound according to the invention shows stability against acid, is beneficial for administration by preparing into normal oral formulation and shows a good druggability.

EXAMPLE

The following specific examples are used to further illustrate the technical solutions of the invention. It is understood that these Example are provided for the purpose of illustration of the protection scope only rather any limitation thereto.

Synthesis Example

Example 1: Preparation of 3-dimethylamino-1-phenyl-1-acetone Hydrochloride

Acetophenone (12.0 g, 0.1 mol), dimethylamine hydrochloride (9.8 g, 0.12 mol), paraformaldehyde (6.0 g, 0.2 mol) and isopropanol (100 mL) were placed in a 250 mL three neck flask, to which was added 2 mL of hydrochloric acid and the reaction mixture was refluxed for 8 h. The reaction was stopped and the reaction mixture was cooled to room temperature. White solid was obtained after sucking filtration to give 17.4 g of 3-dimethylamino-1-phenyl-1-acetone hydrochloride, yield 87%.

Example 2: Preparation of 3-(dimethylamino)-1-phenyl-1-propanol 3-dimethylamino-1-phenyl-1-acetone hydrochloride (10.0 g, 50 mmol) was dissolved in methanol (50 mL). After pH was adjusted to pH=12-13 with sodium hydroxide solution (5%), sodium borohydride (2.3 g, 60 mmol) was added in portions under ice bath. After addition, the reaction mixture was stirred at room temperature for 1 h. The reaction liquid was concentrated, added with water (100 mL), extracted with ethyl acetate, washed with water, dried and concentrated to give 7.9 g of 3-(dimethylamino)-1-phenyl-1-propanol as colorless liquid, yield 96%.

Example 3: Preparation of 3-[(benzo[d][1,3]dioxolan-4-yl)-oxy]-N,N-dimethyl-3-phenylpropylamine oxalate (Corresponding to Compound 1)

3-(dimethylamino)-1-phenyl-1-propanol (2.0 g, 12 mmol), 4-fluorobenzo[1,3]dioxolane (2.5 g, 18 mmol), potassium hydroxide (1.0 g, 18 mmol) and dimethyl sulfoxide (30 mL) were placed in a 100 mL single neck flask, which was reacted for 4 h at 85° C. The reaction liquid was cooled to room temperature, added with water (100 mL), extracted with ethyl acetate, washed with water, dried, concentrated, isolated with column chromatography (eluent: dichloromethane:methanol=10:1) to give light yellow oil. The free base was treated with appropriate amount of oxalic acid to give 2.1 g of 3-[(benzo[d][1,3]dioxolan-4-yl)-oxy]-N,N-dimethyl-3-phenylpropylamine oxalate as white solid, yield 47%, mp: 131-132° C.

$^1$H NMR (400 MHz, DMSO-d$_6$) $\delta_{ppm}$: 2.15-2.30 (2H, m, CHC$\underline{H}_2$), 2.72 (6H, s, CH$_3$×2), 3.08-3.16 (2H, m, C$\underline{H}_2$N), 5.46-5.48 (1H, m, CH), 5.96-5.99 (2H, s×2, OC$\underline{H}_2$O), 6.47-6.64 (3H, m, Ar—H), 7.39-7.41 (5H, m, Ar—H)

MS (ESI, m/z): 300 (M+H)$^+$

Example 4: Preparation of 3-[(benzo[d][1,3]dioxolan-4-yl)-oxy]-N-methyl-3-phenylpropylamine oxalate (Corresponding to Compound 2)

3-[(benzo[d][1,3]dioxolan-4-yl)-oxy]-N,N-dimethyl-3-phenylpropylamine (2.0 g, 7 mmol) was dissolved in toluene (50 mL), to which was added diisopropylethylamine (0.2 g). At an elevated temperature of 60° C., a solution of phenyl chloroformate (1.5 g, 10 mmol) in toluene (10 mL) was added dropwise. After addition, the reaction was performed at the same temperature for about 3 h and then the temperature was lowered. The reaction liquid was washed with saturated sodium bicarbonate solution (50 mL), hydrochloric acid solution (5%, 50 mL) and water (100 mL) respectively and toluene was distilled off under reduced pressure. The residue was dissolved in dimethyl sulfoxide (30 mL) and sodium hydroxide solution was added (2.0 g in 10 mL). The temperature was raised to 85° C. and the reaction was performed for about 8 h. After the reaction mixture was cooled to room temperature, it was added with water, extracted with ethyl acetate, washed with water, dried, concentrated to give light yellow oil. The crude was treated with an appropriate amount of oxalic acid to give 1.8 g of 3-[(benzo[d][1,3]dioxolan-4-yl)-oxy]-N-methyl-3-phenylpropylamine oxalate as white solid, yield 71%. mp: 139-141° C.

$^1$H NMR (400 MHz, DMSO-d$_6$) $\delta_{ppm}$: 2.12-2.24 (2H, m. CHC$\underline{H}_2$), 2.56 (3H, s, CH$_3$), 2.98-3.02 (2H, m, C$\underline{H}_2$N), 5.49-5.53 (1H, m, CH), 5.96-5.99 (2H, s×2, OC$\underline{H}_2$O), 6.47-6.64 (3H, m, Ar—H), 7.37-7.39 (5H, m, Ar—H)

MS (ESI, m/z): 286 (M+H)$^+$

Example 5: Preparation of 3-(dimethylamino)-1-(4-fluorobenzene)-1-acetone

According to the procedures in Example 1, 4-fluoroacetophenone was reacted with dimethylamine hydrochloride and paraformaldehyde to give 3-(dimethylamino)-1-(4-fluorobenzene)-1-acetone as colorless liquid, yield 78%.

Example 6: Preparation of 3-(dimethylamino)-1-(4-fluorobenzene)-1-propanol

According to the procedures in Example 2, 3-(dimethylamino)-1-(4-fluorobenzene)-1-acetone was reacted with sodium borohydride to give 3-(dimethylamino)-1-(4-fluorobenzene)-1-propanol as colorless liquid, yield 94%.

Example 7: Preparation of 3-[(benzo[d][1,3]dioxolan-4-yl)-oxy]-3-(4-fluorophenyl)-N,N-dimethylpropylamine oxalate (Corresponding to Compound 3)

According to the procedures in Example 3, 3-(dimethylamino)-1-(4-fluorobenzene)-1-propanol was reacted with 4-fluorobenzo[1,3]dioxolane and the product was purified with column chromatography and salified with oxalic acid to give 3-[(benzo[d][1,3]dioxolan-4-yl)-oxy]-3-(4-fluorophenyl)-N,N-dimethylpropylamine oxalate as white solid, yield 44%, melting point: 111-114° C.

$^1$H NMR (400 MHz, DMSO-d$_6$) $\delta_{ppm}$: 2.16-2.33 (2H, m, CH$_2$), 2.74 (6H, s, CH$_3$×2), 3.08-3.19 (2H, m, CH$_2$N), 5.49-5.50 (1H, m, CH), 5.96-5.99 (2H, s×2, OCH$_2$O), 6.51-6.65 (3H, m, Ar—H), 7.20-7.46 (4H, m, Ar—H)

MS (ESI, m/z): 318 (M+H)$^+$

Example 8: Preparation of 3-[(benzo[d][1,3]dioxolan-4-yl)-oxy]-3-(4-fluorophenyl)-N-methylpropylamine oxalate (Corresponding to Compound 4)

According to the procedures in Example 4, 3-[(benzo[d][1,3]dioxolan-4-yl)-oxy]-3-(4-fluorophenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(4-fluorophenyl)-N-methylpropylamine oxalate as white solid, yield 65%, melting point: 150-151° C.

$^1$H NMR (400 MHz, DMSO-d$_6$) $\delta_{ppm}$: 2.12-2.23 (2H, m, CHCH$_2$), 2.76 (3H, s, CH$_3$), 2.98-3.04 (2H, m, CH$_2$N), 5.58-5.63 (1H, m, CH), 5.95-5.98 (2H, s×2, OCH$_2$O), 6.49-6.66 (3H, m, Ar—H), 7.36-7.39 (4H, m, Ar—H)

MS (ESI, m/z): 304 (M+H)$^+$

Example 9: Preparation of 3-(dimethylamino)-1-(4-chlorobenzene)-1-acetone

According to the procedures in Example 1, 4-chloroacetophenone was reacted with dimethylamine hydrochloride and paraformaldehyde to give 3-(dimethylamino)-1-(4-chlorobenzene)-1-acetone as colorless liquid, yield 82%.

Example 10: Preparation of 3-(dimethylamino)-1-(4-chlorobenzene)-1-propanol

According to the procedures in Example 2, 3-(dimethylamino)-1-(4-chlorobenzene)-1-acetone was reacted with sodium borohydride to give 3-(dimethylamino)-1-(4-chlorobenzene)-1-propanol as colorless liquid, yield 95%.

Example 11: Preparation of 3-[(benzo[d][1,3]dioxolan-4-yl)-oxy]-3-(4-chlorophenyl)-N,N-dimethylpropylamine oxalate (Corresponding to Compound 5)

According to the procedures in Example 3, 3-(dimethylamino)-1-(4-chlorobenzene)-1-propanol was reacted with 4-fluorobenzo[1,3]dioxolane and the product was purified with column chromatography and salified with oxalic acid to give 3-[(benzo[d][1,3]dioxolan-4-yl)-oxy]-3-(4-chlorophenyl)-N,N-dimethylpropylamine oxalate as white solid, yield 53%, melting point: 150-152° C.

$^1$H NMR (400 MHz, DMSO-d$_6$) $\delta_{ppm}$: 2.16-2.35 (2H, m, CHCH$_2$), 2.76 (6H, s, CH$_3$×2), 3.07-3.19 (2H, m, CH$_2$N), 5.49-5.51 (1H, m, CH), 5.96-5.99 (2H, s×2, OCH$_2$O), 6.51-6.66 (3H, m. Ar—H), 7.21-7.46 (4H, m, Ar—H)

MS (ESI, m/z): 334 (M+H)$^+$

Example 12: Preparation of 3-[(benzo[d][1,3]dioxolan-4-yl)-oxy]-3-(4-chlorophenyl)-N-methylpropylamine oxalate (Corresponding to Compound 6)

According to the procedures in Example 4, 3-[(benzo[d][1,3]dioxolan-4-yl)-oxy]-3-(4-chlorophenyl)-N,N-dimethylpropylamine was reacted with phenyl chloroformate. After reaction, hydrolysis decarboxylation was performed with sodium hydroxide and the product was salified to give 3-[(benzo[d][1,3]dioxolan-4-yl)-oxy]-3-(4-chlorophenyl)-N-methylpropylamine oxalate as white solid, yield 74%, melting point: 146-148° C.

$^1$H NMR (400 MHz, DMSO-d$_6$) $\delta_{ppm}$: 2.12-2.24 (2H, m, CHCH$_2$), 2.76 (3H, s, CH$_3$), 2.98-3.05 (2H, m, CH$_2$N), 5.56-5.63 (1H, m, CH), 5.94-5.98 (2H, s×2, OCH$_2$O), 6.47-6.66 (3H, m, Ar—H), 7.35-7.39 (4H, m, Ar—H)

MS (ESI, m/z): 320 (M+H)$^+$

Example 13: Preparation of 3-(dimethylamino)-1-(3-chlorobenzene)-1-acetone

According to the procedures in Example 1, 3-chloroacetophenone was reacted with dimethylamine hydrochloride and paraformaldehyde to give 3-(dimethylamino)-1-(3-chlorobenzene)-1-acetone as colorless liquid, yield 85%.

Example 14: Preparation of 3-(dimethylamino)-1-(3-chlorobenzene)-1-propanol

According to the procedures in Example 2, 3-(dimethylamino)-1-(3-chlorobenzene)-1-acetone was reacted with sodium borohydride to give 3-(dimethylamino)-1-(3-chlorobenzene)-1-propanol as colorless liquid, yield 95%.

Example 15: Preparation of 3-[(benzo[d][1,3]dioxolan-4-yl)-oxy]-3-(3-chlorophenyl)-N,N-dimethylpropylamine oxalate (Corresponding to Compound 7)

According to the procedures in Example 3, 3-(dimethylamino)-1-(3-chlorobenzene)-1-propanol was reacted with 4-fluorobenzo[1,3]dioxolane, and the product was purified with column chromatography and salified with oxalic acid to give 3-[(benzo[d][1,3]dioxolan-4-yl)-oxy]-3-(3-chlorophenyl)-N,N-dimethylpropylamine oxalate as white solid, yield 60%, melting point: 146-148° C.

$^1$H NMR (400 MHz, DMSO-d$_6$) $\delta_{ppm}$: 2.19-2.33 (2H, m, CHCH$_2$), 2.74 (6H, s, CH$_3$×2), 3.11-3.19 (2H, m, CH$_2$N), 5.50-5.51 (1H, m, CH), 5.97-5.99 (2H, s×2. OCH$_2$O), 6.51-6.67 (3H, m, Ar—H), 7.36-7.48 (4H, m, Ar—H)

MS (ESI, m/z): 334 (M+H)$^+$

Example 16: Preparation of 3-[(benzo[d][1,3]dioxolan-4-yl)-oxy]-3-(3-chlorophenyl)-N-methylpropylamine oxalate (Corresponding to Compound 8)

According to the procedures in Example 4, 3-[(benzo[d][1,3]dioxolan-4-yl)-oxy]-3-(3-chlorophenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(3-chlorophenyl)-N-methylpropylamine oxalate as white solid, yield 55%, melting point: 134-137° C.

$^1$H NMR (400 MHz. DMSO-d$_6$) $\delta_{ppm}$: 2.13-2.23 (2H, m, CHCH$_2$), 2.76 (3H, s, CH$_3$), 2.98-3.05 (2H, m, CH$_2$N), 5.58-5.64 (1H, m, CH), 5.96-5.99 (2H, s×2, OCH$_2$O), 6.50-6.67 (3H, m, Ar—H), 7.36-7.38 (4H, m, Ar—H)

MS (ESI, m/z): 320 (M+H)$^+$

Example 17: Preparation of 3-(dimethylamino)-1-(3-fluorobenzene)-1-acetone

According to the procedures in Example 1, 3-fluoroacetophenone was reacted with dimethylamine hydrochloride and paraformaldehyde to give 3-(dimethylamino)-1-(3-fluorobenzene)-1-acetone as colorless liquid, yield 83%.

Example 18: Preparation of 3-(dimethylamino)-1-(3-fluorobenzene)-1-propanol

According to the procedures in Example 2, 3-(dimethylamino)-1-(3-fluorobenzene)-1-acetone was reacted with sodium borohydride to give 3-(dimethylamino)-1-(3-fluorobenzene)-1-propanol as colorless liquid, yield 93%.

Example 19: Preparation of 3-[(benzo[d][1,3]dioxolan-4-yl)-oxy]-3-(3-fluorophenyl)-N,N-dimethylpropylamine oxalate (Corresponding to Compound 9)

According to the procedures in Example 3, 3-(dimethylamino)-1-(3-fluorobenzene)-1-propanol was reacted with 4-fluorobenzo[1,3]dioxolane, and the product was purified with column chromatography and salified with oxalic acid to give 3-[(benzo[d][1,3]dioxolan-4-yl)-oxy]-3-(3-fluorophenyl)-N,N-dimethylpropylamine oxalate as white solid, yield 48%, melting point: 129-131° C.
$^1$H NMR (400 MHz, DMSO-d$_6$) δ$_{ppm}$: 2.15-2.32 (2H, m, CHC$\underline{H}_2$), 2.76 (6H, s, CH$_3$×2), 3.08-3.17 (2H, m, C$\underline{H}_2$N), 5.50-5.51 (1H, m, CH), 5.97-6.01 (2H, s×2, OC$\underline{H}_2$O), 6.54-6.69 (3H, m, Ar—H), 7.36-7.48 (4H, m, Ar—H)

Example 20: Preparation of 3-[(benzo[d][1,3]dioxolan-4-yl)-oxy]-3-(3-fluorophenyl)-N-methylpropylamine oxalate (Corresponding to Compound 10)

According to the procedures in Example 4, 3-[(benzo[d][1,3]dioxolan-4-yl)-oxy]-3-(3-fluorophenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(3-fluorophenyl)-N-methylpropylamine oxalate as white solid, yield 65%, melting point: 162-164° C.
$^1$H NMR (400 MHz, DMSO-d$_6$) δ$_{ppm}$: 2.13-2.23 (2H, m, CHC$\underline{H}_2$), 2.76 (3H, s, CH$_3$), 2.98-3.06 (2H, m, C$\underline{H}_2$N), 5.58-5.68 (1H, m, CH), 5.95-5.98 (2H, s×2, OC$\underline{H}_2$O), 6.50-6.67 (3H, m, Ar—H), 7.46-7.48 (4H, m, Ar—H)

Example 21: Preparation of 3-(dimethylamino)-1-(3-methoxybenzene)-1-acetone

According to the procedures in Example 1, 3-methoxylacetophenone was reacted with dimethylamine hydrochloride and paraformaldehyde to give 3-(dimethylamino)-1-(3-methoxylbenzene)-1-acetone as colorless liquid, yield 68%.

Example 22: Preparation of 3-(dimethylamino)-1-(3-methoxybenzene)-1-propanol

According to the procedures in Example 2, 3-(dimethylamino)-1-(3-methoxybenzene)-1-acetone was reacted with sodium borohydride to give 3-(dimethylamino)-1-(3-methoxybenzene)-1-propanol as colorless liquid, yield 85%.

Example 23: Preparation of 3-[(benzo[d][1,3]dioxolan-4-yl)-oxy]-3-(3-methoxylphenyl)-N,N-dimethylpropylamine oxalate (Corresponding to Compound 11)

According to the procedures in Example 3, 3-(dimethylamino)-1-(3-methoxylbenzene)-1-propanol was reacted with 4-fluorobenzo[1,3]dioxolane, and the product was purified with column chromatography and salified with oxalic acid to give 3-[(benzo[d][1,3]dioxolan-4-yl)-oxy]-3-(3-methoxylphenyl)-N,N-dimethylpropylamine oxalate as white solid, yield 35%, melting point: 139-141° C.
$^1$H NMR (400 MHz, DMSO-d$_6$) δ$_{ppm}$: 2.09-2.22 (2H, m, CHC$\underline{H}_2$), 2.66 (6H, s, CH$_3$×2), 3.08-3.17 (2H, m, C$\underline{H}_2$N), 3.65 (3H, s, OCH$_3$), 5.55-5.58 (1H, m, CH), 5.97-6.01 (2H, s×2, OC$\underline{H}_2$O), 6.53-6.68 (3H, m, Ar—H), 7.26-7.38 (4H, m, Ar—H)
MS (ESI, m/z): 330 (M+H)$^+$ Example 24: Preparation of 3-[(benzo[d][1,3]dioxolan-4-yl)-oxy]-3-(3-methoxylphenyl)-N-methylpropylamine oxalate (Corresponding to Compound 12)

According to the procedures in Example 4, 3-[(benzo[d][1,3]dioxolan-4-yl)-oxy]-3-(3-methoxylphenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(3-methoxylphenyl)-N-methylpropylamine oxalate as white solid, yield 45%, melting point: 154-158° C.
$^1$H NMR (400 MHz, DMSO-d$_6$) δ$_{ppm}$: 2.09-2.13 (2H, m, CHC$\underline{H}_2$), 2.86 (3H, s, CH$_3$), 2.98-3.07 (2H, m, C$\underline{H}_2$N), 3.79 (3H, s, OCH$_3$), 5.59-5.69 (1H, m, CH), 5.95-5.99 (2H, s×2, OC$\underline{H}_2$O), 6.53-6.68 (3H, m, Ar—H), 7.43-7.47 (4H, m, Ar—H)
MS (ESI, m/z): 316 (M+H)$^+$ Example 25: Preparation of 3-(dimethylamino)-1-(3-methylbenzene)-1-acetone According to the procedures in Example 1, 4-fluoroacetophenone was reacted with dimethylamine hydrochloride and paraformaldehyde to give 3-(dimethylamino)-1-(3-methylbenzene)-1-acetone as colorless liquid, yield 78%.

Example 26: Preparation of 3-(dimethylamino)-1-(3-methylbenzene)-1-propanol

According to the procedures in Example 2, 3-(dimethylamino)-1-(3-methylbenzene)-1-acetone was reacted with sodium borohydride to give 3-(dimethylamino)-1-(3-methylbenzene)-1-propanol as colorless liquid, yield 90%.

Example 27: Preparation of 3-[(benzo[d][1,3]dioxolan-4-yl)-oxy]-3-(3-methylphenyl)-N,N-dimethylpropylamine oxalate (Corresponding to Compound 13)

According to the procedures in Example 3, 3-(dimethylamino)-1-(3-methylbenzene)-1-propanol was reacted with 4-fluorobenzo[1,3]dioxolane, and the product was purified with column chromatography and salified with oxalic acid to give 3-[(benzo[d][1,3]dioxolan-4-yl)-oxy]-3-(3-methylphenyl)-N,N-dimethylpropylamine oxalate as white solid, yield 67%, melting point: 128-131° C.
$^1$H NMR (400 MHz, DMSO-d$_6$) δ$_{ppm}$: 2.13-2.32 (2H, m, CHC$\underline{H}_2$), 2.38 (3H, s, PhC$\underline{H}_3$), 2.68 (6H, s, CH$_3$×2), 3.08-3.17 (2H, m, C$\underline{H}_2$N), 5.55-5.58 (1H, m, CH), 5.97-6.01 (2H, s×2, OC$\underline{H}_2$O), 6.53-6.68 (3H, m, Ar—H), 7.26-7.36 (4H, m, Ar—H)
MS (ESI, m/z): 314 (M+H)$^+$

Example 28: Preparation of 3-[(benzo[d][1,3]dioxolan-4-yl)-oxy]-3-(3-methylphenyl)-N-methylpropylamine oxalate (Corresponding to Compound 14)

According to the procedures in Example 4, 3-[(benzo[d][1,3]dioxolan-4-yl)-oxy]-3-(3-methylphenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(3-methylphenyl)-N-methylpropylamine oxalate as white solid, yield 76%, melting point: 141-144° C.

$^1$H NMR (400 MHz, DMSO-d$_6$) $\delta_{ppm}$: 2.11-2.25 (2H, m, CH$\underline{CH_2}$), 2.86 (3H, s, CH$_3$), 2.98-3.07 (2H, m, $\underline{CH_2}$N), 2.42 (3H, s, Ph$\underline{CH_3}$), 5.59-5.69 (1H, m, CH), 5.95-5.99 (2H, s×2, O$\underline{CH_2}$O), 6.52-6.68 (3H, m, Ar—H), 7.43-7.47 (4H, m, Ar—H)

MS (ESI, m/z): 300 (M+H)$^+$

Example 29: Preparation of 3-(dimethylamino)-1-(2-fluorobenzene)-1-acetone

According to the procedures in Example 1, 2-fluoroacetophenone was reacted with dimethylamine hydrochloride and paraformaldehyde to give 3-(dimethylamino)-1-(2-fluorobenzene)-1-acetone as colorless liquid, yield 80%.

Example 30: Preparation of 3-(dimethylamino)-1-(2-fluorobenzene)-1-propanol

According to the procedures in Example 2, 3-(dimethylamino)-1-(2-fluorobenzene)-1-acetone was reacted with sodium borohydride to give product as colorless liquid, yield 95%.

Example 31: Preparation of 3-[(benzo[d][1,3]dioxolan-4-yl)-oxy]-3-(2-fluorophenyl)-N,N-dimethylpropylamine oxalate (Corresponding to Compound 15)

According to the procedures in Example 3, 3-(dimethylamino)-1-(2-fluorobenzene)-1-propanol was reacted with 4-fluorobenzo[1,3]dioxolane, and the product was purified with column chromatography and salified with oxalic acid to give 3-[(benzo[d][1,3]dioxolan-4-yl)-oxy]-3-(2-fluorophenyl)-N,N-dimethylpropylamine oxalate as white solid, yield 58%, melting point: 138-140° C.

$^1$H NMR (400 MHz, DMSO-d$_6$) $\delta_{ppm}$: 2.16-2.33 (2H, m, CH$\underline{CH_2}$), 2.76 (6H, s, CH$_3$×2), 3.08-3.19 (2H, m, $\underline{CH_2}$N), 5.49-5.50 (1H, m, CH), 5.96-5.99 (2H, s×2, O$\underline{CH_2}$O), 6.53-6.67 (3H, m, Ar—H), 7.22-7.48 (4H, m, Ar—H)

MS (ESI, m/z): 318 (M+H)$^+$

Example 32: Preparation of 3-[(benzo[d][1,3]dioxolan-4-yl)-oxy]-3-(2-fluorophenyl)-N-methylpropylamine oxalate (Corresponding to Compound 16)

According to the procedures in Example 4, 3-[(benzo[d][1,3]dioxolan-4-yl)-oxy]-3-(2-fluorophenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(2-fluorophenyl)-N-methylpropylamine oxalate as white solid, yield 40%, melting point: 167-169° C.

$^1$H NMR (400 MHz. DMSO-d$_6$) $\delta_{ppm}$: 2.12-2.23 (2H, m, CH$\underline{CH_2}$), 2.73 (3H, s, CH$_3$), 2.98-3.04 (2H, m, $\underline{CH_2}$N), 5.58-5.63 (1H, m, CH), 5.95-5.98 (2H, s×2, O$\underline{CH_2}$O), 6.49-6.66 (3H, m, Ar—H), 7.36-7.39 (4H, m, Ar—H)

MS (ESI, m/z): 304 (M+H)$^+$

Example 33: Preparation of 3-(dimethylamino)-1-(3,4-dichlorobenzene)-1-acetone According to the procedures in Example 1, 4-fluoroacetophenone was reacted with dimethylamine hydrochloride and paraformaldehyde to give 3-(dimethylamino)-1-(3,4-dichlorobenzene)-1-acetone as colorless liquid, yield 77%.

Example 34: Preparation of 3-(dimethylamino)-1-(3,4-dichlorobenzene)-1-propanol According to the procedures in Example 2, 3-(dimethylamino)-1-(2-fluorobenzene)-1-acetone was reacted with sodium borohydride to give 3-(dimethylamino)-1-(3,4-dichlorobenzene)-1-propanol as colorless liquid, yield 85%.

Example 35: Preparation of 3-[(benzo[d][1,3]dioxolan-4-yl)-oxy]-3-(3,4-dichlorophenyl)-N,N-dimethylpropylamine oxalate (Corresponding to Compound 17)

According to the procedures in Example 3, 3-(dimethylamino)-1-(3,4-dichlorobenzene)-1-propanol was reacted with 4-fluorobenzo[1,3]dioxolane, and the product was purified with column chromatography and salified with oxalic acid to give 3-[(benzo[d][1,3]dioxolan-4-yl)-oxy]-3-(3,4-dichlorophenyl)-N,N-dimethylpropylamine oxalate as white solid, yield 36%, melting point: 174-177° C.

$^1$H NMR (400 MHz, DMSO-d$_6$) $\delta_{ppm}$: 2.12-2.23 (2H, m, CH$\underline{CH_2}$), 2.76 (6H, s, CH$_3$×2), 3.08-3.18 (2H, m, $\underline{CH_2}$N), 5.49-5.53 (1H, m, CH), 5.96-6.01 (2H, s×2, O$\underline{CH_2}$O), 6.53-6.67 (3H, m. Ar—H), 7.22-7.32 (3H, m, Ar—H)

MS (ESI, m/z): 368 (M+H)$^+$

Example 36: Preparation of 3-[(benzo[d][1,3]dioxolan-4-yl)-oxy]-3-(3,4-dichlorophenyl)-N-methylpropylamine oxalate (Corresponding to Compound 18)

According to the procedures in Example 4, 3-[(benzo[d][1,3]dioxolan-4-yl)-oxy]-3-(3,4-dichlorophenyl)-N,N-dimethylpropylamine was reacted with phenyl chloroformate. After reaction, hydrolysis decarboxylation was performed with sodium hydroxide and the product was salified with oxalic acid to give 3-[(benzo[d][1,3]dioxolan-4-yl)-oxy]-3-(3,4-dichlorophenyl)-N-methylpropylamine oxalate as white solid, yield 43%, melting point: 183-185° C.

$^1$H NMR (400 MHz, DMSO-d$_6$) $\delta_{ppm}$: 2.13-2.24 (2H, m, CH$\underline{CH_2}$), 2.73 (3H, s, CH$_3$), 2.97-3.05 (2H, m, $\underline{CH_2}$N), 5.58-5.63 (1H, m, CH), 5.95-5.98 (2H, s>2, O$\underline{CH_2}$O), 6.49-6.69 (3H, m, Ar—H), 7.36-7.39 (3H, m, Ar—H)

MS (ESI, m/z): 354 (M+H)$^+$

Biological Efficacy Example

In Example 37-39, the compound according to the invention in the form of oxalate was used.

Example 37: In Vivo Antidepressant Activity Study in Animal

Mice tail suspension test and mice forced swimming test in "acquired despair experiment" were used to preliminarily investigate in vivo antidepressant activity of the compound according to the invention, wherein duloxetine was used as positive control drug.

TABLE 1

Effect of gavage administration of the compound according to the invention on immobilized time of mice tail suspension

| dosage (mg/kg, i.g.) | duloxetine | compound 2 | compound 3 | compound 4 | compound 12 | compound 13 |
|---|---|---|---|---|---|---|
| | | | immobilized time (s) | | | |
| 0 | | | 73.2 ± 42.3 | | | |
| 5 | NA | 44.3 ± 34.5 | 22.0 ± 28.2** | 21.4 ± 12.8** | 64.1 ± 24.5 | 71.3 ± 32.7 |
| 10 | 34.7 ± 42.3 | 8.2 ± 13.7** | 9.2 ± 13.3** | 29.6 ± 13.1** | 33.0 ± 15.6** | 29.8 ± 21.3** |
| 20 | 17.8 ± 18.5** | NA | NA | NA | NA | NA |

**$P < 0.01$: as compared to blank control group;
NA: not available

TABLE 2

Effect of gavage administration of the compound according to the invention on immobilized time of mice swimming

| dosage (mg/kg, i.g.) | duloxetine | compound 2 | compound 3 | compound 4 | compound 12 | compound 13 |
|---|---|---|---|---|---|---|
| | | | immobilized time (s) | | | |
| 0 | | | 113.7 ± 62.9 | | | |
| 5 | NA | 38.9 ± 34.5** | 42.0 ± 56.1** | 74.1 ± 36.8 * | 92.0 ± 45.5 | 87.9 ± 55.6 |
| 10 | 76.0 ± 57.8 | 28.6 ± 19.3** | 31.0 ± 54.2** | 60.1 ± 42.2** | 58.2 ± 45.3** | 60.2 ± 38.6** |
| 20 | 41.2 ± 33.3** | NA | NA | NA | NA | NA |

**$P < 0.01$: as compared to blank control group;
NA: not available

According to Table 1 and 2, in mice tail suspension test and forced swimming test, the compound according to the invention could significantly reduce the immobilized time caused by despair. The shorter the immobilized time is, the stronger the antidepressant activity is. Moreover, at the same dosage, the compound according to the invention showed significantly stronger antidepressant activity than duloxetine.

Example 38: Therapeutic Index Evaluation

Therapeutic index is an indicator for the safety of a drug and shown as half lethal dose (LD50)/half effective dose (ED50). The results were shown as follows.

TABLE 3

Therapeutic indexes of the compound according to the invention

| compound | tail suspension ED50 (mg/kg) | swimming ED50 (mg/kg) | LD50 (mg/kg) | therapeutic index (tail suspension) | therapeutic index (swimming) |
|---|---|---|---|---|---|
| duloxetine | 5.96 | 4.94 | 489.2 | 82.1 | 98.9 |
| ammuxetine | 3.89 | 2.58 | 177.8 | 45.7 | 68.9 |
| compound 2 | 7.06 | 2.0 | 177.6 | 25.2 | 88.8 |
| compound 3 | 4.32 | 2.28 | 354.9 | 82.2 | 155.6 |
| compound 12 | 8.57 | 5.28 | 320.4 | 37.4 | 60.7 |

According to Table 3, therapeutic indexes of compound 3 (82.2 and 155.6) are higher than duloxetine (82.1 and 98.8) and ammuxetine (45.7 and 68.9), showing a better safety over duloxetine and ammuxetine.

Example 39 Acid Stability Evaluation

The compound according to the invention was incubated in diluted hydrochloric acid (0.1 mol/L) at 37° C. for 2 h to test the decomposition of the compound (shown as %) and the results were shown as follows.

TABLE 4

Stability of the compound according to the invention in acid medium

| compound | ratio of the compound after incubation in diluted hydrochloric acid at 37° C. for 2 h (%) |
|---|---|
| duloxetine | 18 |
| ammuxetine | 44 |
| compound 2 | 99 |
| compound 3 | 99 |
| compound 4 | 99 |

TABLE 4-continued

Stability of the compound according to the invention in acid medium

| compound | ratio of the compound after incubation in diluted hydrochloric acid at 37° C. for 2 h (%) |
|---|---|
| compound 12 | 99 |
| compound 13 | 99 |

According to Table 4, the compound according to the invention has a better acid stability than duloxetine and ammuxetine, showing a wider selection range for dosage form.

Formulation Example

Example 40: Tablet

| Active Ingredient (anyone of the compounds 1~18 or pharmaceutically acceptable salt thereof) | 100 mg |
|---|---|
| microcrystalline cellulose | 50 mg |
| lactose | 100 mg |
| Povidone K30 | 9 mg |
| carboxymethyl starch sodium | 12 mg |
| silica | 2.5 mg |
| magnesium stearate | 1.5 mg |

The raw excipients were sieved with 80 mesh for use. The prescription doses of active ingredient, microcrystalline cellulose, lactose, Povidone K30 were weighed and introduced into a high speed mixing granulator, whereby they were mixed uniformly at low speed. A suitable amount of purified water was added, the stirring was performed at low speed, and high speed shear granulation was carried out. The wet granules were dried at 60° C. for 3 h, and sieved with 24 mesh. The prescription doses of carboxymethyl starch sodium, silica and magnesium stearate were added for mixing totally. The compression was performed in a rotary tablet press.

Example 41: Capsule (230 mg)

| Active Ingredient (anyone of the compounds 1~18 or pharmaceutically acceptable salt thereof) | 100 mg |
|---|---|
| lactose | 80 mg |
| starch | 40 mg |
| Povidone K30 | 7 mg |
| silica | 2 mg |
| magnesium stearate | 1 mg |

The raw excipients were sieved with 80 mesh for use. The prescription doses of active ingredient, lactose, starch, Povidone K30 were weighed and introduced into a high speed mixing granulator, whereby they were mixed uniformly at low speed. A suitable amount of purified water was added, the stirring was performed at low speed, and high speed shear granulation was carried out. The wet granules were dried at 60° C. for 3 h. and sieved with 24 mesh. The prescription doses of silica and magnesium stearate were added for mixing totally. The capsules were filled in a capsule filling machine.

Structures of the compounds 1~18 according to the invention are shown as follows:

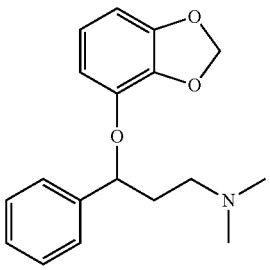

compound 1

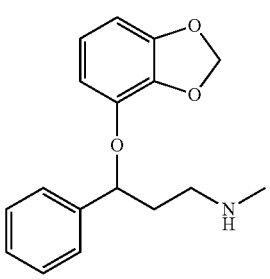

compound 2

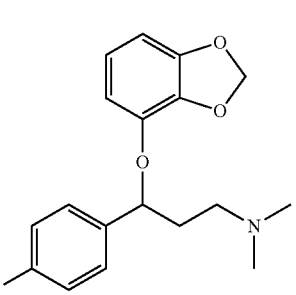

compound 3

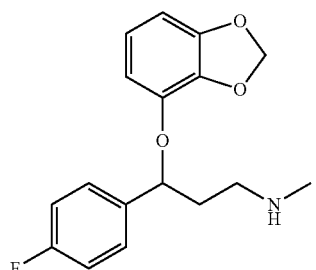

compound 4

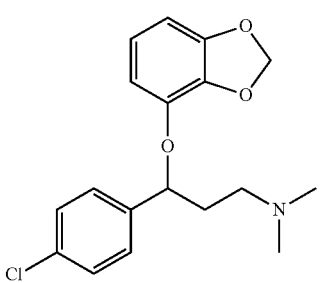

compound 5 compound 6
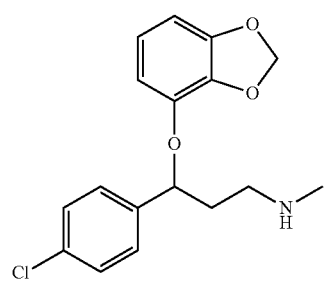
compound 7
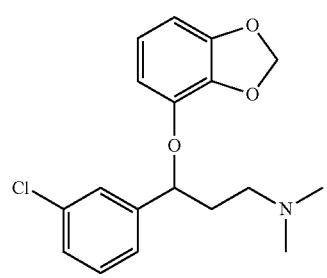
compound 8
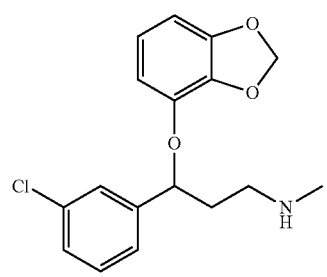
compound 9
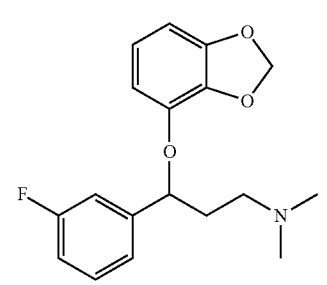
compound 10
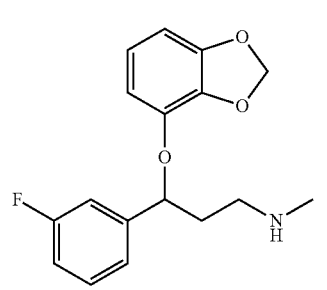
compound 11
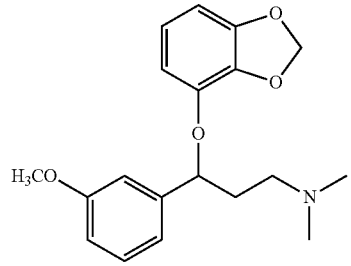
compound 12
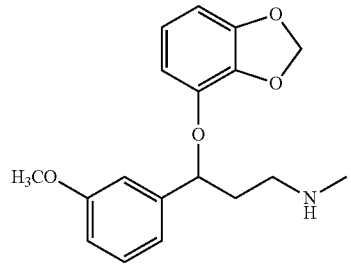
compound 13
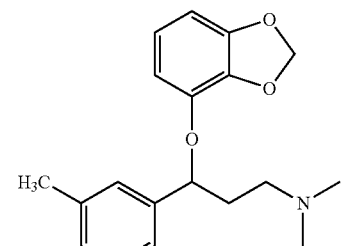
compound 14
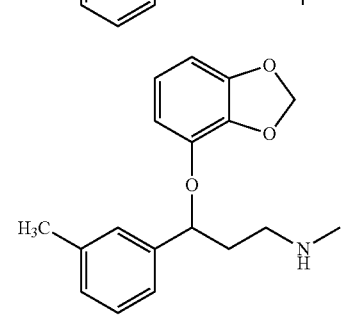
compound 15
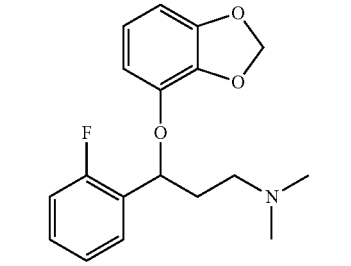
compound 16
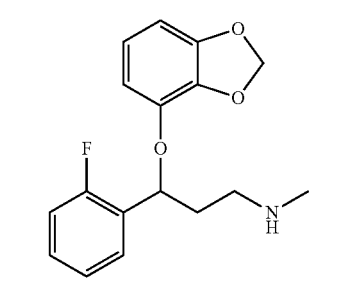

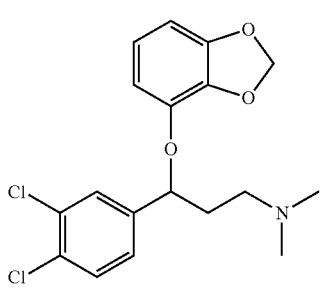

compound 17

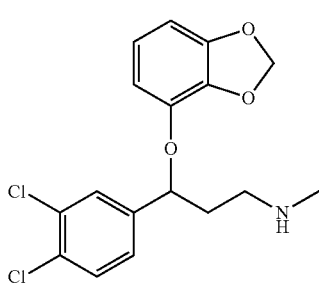

compound 18

The invention claimed is:

1. A compound of formula I, an optical isomer thereof or a pharmaceutically acceptable salt thereof:

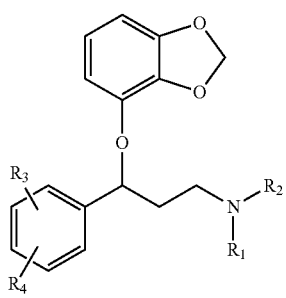

I wherein, $R_1$ and $R_2$ are independently hydrogen or $C_{1-5}$ alkyl; and
$R_3$ and $R_4$ are independently hydrogen, halogen, substituted or unsubstituted $C_{1-5}$ alkyl or $C_{1-3}$ alkoxyl.

2. The compound of formula I according to claim 1 or the pharmaceutically acceptable salt thereof, wherein the halogen is F, Cl, Br or I.

3. The compound of formula I according to claim 1 or the pharmaceutically acceptable salt thereof, wherein the unsubstituted $C_{1-5}$ alkyl in $R_3$ and $R_4$ is methyl, ethyl or isopropyl.

4. The compound of formula I according to claim 1 or the pharmaceutically acceptable salt thereof, wherein the substituted $C_{1-5}$ alkyl is trifluoromethyl.

5. The compound of formula I according to claim 1 or the pharmaceutically acceptable salt thereof, wherein the $C_{1-3}$ alkoxyl is methoxyl or ethoxyl.

6. The compound of formula I according to claim 1 or the pharmaceutically acceptable salt thereof, wherein the pharmaceutically acceptable salt is selected from the group consisting of oxalate, hydrochloride, hydrobromide, hydriodate, nitrate, sulfate, bisulfate, phosphate, acid phosphate, acetate, lactate, citrate, tartrate, maleate, fumarate, methanesulfonate, gluconate, saccharate, benzoate, ethanesulfonate, benzenesulfonate and p-toluenesulfonate.

7. The compound of formula I according to claim 1 or the pharmaceutically acceptable salt thereof, wherein the compound of formula I is selected from;

3-[(benzo[d][1,3]dioxolan-4-yl)-oxy]-N,N-dimethyl-3-phenylpropylamine;
3-[(benzo[d][1,3]dioxolan-4-yl)-oxy]-N-methyl-3-phenylpropylamine;
3-[(benzo[d][1,3]dioxolan-4-yl)-oxy]-3-(4-fluorophenyl)-N,N-dimethylpropylamine;
3-[(benzo[d][1,3]dioxolan-4-yl)-oxy]-3-(4-fluorophenyl)-N-methylpropylamine;
3-[(benzo[d][1,3]dioxolan-4-yl)-oxy]-3-(4-chlorophenyl)-N,N-dimethylpropylamine;
3-[(benzo[d][1,3]dioxolan-4-yl)-oxy]-3-(4-chlorophenyl)-N-methylpropylamine;
3-[(benzo[d][1,3]dioxolan-4-yl)-oxy]-3-(3-chlorophenyl)-N,N-dimethylpropylamine;
3-[(benzo[d][1,3]dioxolan-4-yl)-oxy]-3-(3-chlorophenyl)-N-methylpropylamine;
3-[(benzo[d][1,3]dioxolan-4-yl)-oxy]-3-(3-fluorophenyl)-N,N-dimethylpropylamine;
3-[(benzo[d][1,3]dioxolan-4-yl)-oxy]-3-(3-fluorophenyl)-N-methylpropylamine;
3-[(benzo[d][1,3]dioxolan-4-yl)-oxy]-3-(3-methoxyphenyl)-N,N-dimethylpropylamine;
3-[(benzo[d][1,3]dioxolan-4-yl)-oxy]-3-(3-methoxyphenyl)-N-methylpropylamine;
3-[(benzo[d][1,3]dioxolan-4-yl)-oxy]-3-(3-methylphenyl)-N,N-dimethylpropylamine;
3-[(benzo[d][1,3]dioxolan-4-yl)-oxy]-3-(3-methylphenyl)-N-methylpropylamine;
3-[(benzo[d][1,3]dioxolan-4-yl)-oxy]-3-(2-fluorophenyl)-N,N-dimethylpropylamine;
3-[(benzo[d][1,3]dioxolan-4-yl)-oxy]-3-(2-fluorophenyl)-N-methylpropylamine;
3-[(benzo[d][1,3]dioxolan-4-yl)-oxy]-3-(3,4-dichlorophenyl)-N,N-dimethylpropylamine; and
3-[(benzo[d][1,3]dioxolan-4-yl)-oxy]-3-(3,4-dichlorophenyl)-N-methylpropylamine;

and oxalate of the above compounds.

8. A pharmaceutical composition, comprising the compound according to claim 1 or the pharmaceutically acceptable salt thereof in a therapeutically effective amount and pharmaceutically acceptable carrier and/or excipient.

9. A method for treating depression, comprising administering to a subject in need thereof the compound or a pharmaceutically acceptable salt according to claim 1.

10. A method for treating depression, comprising administering to a subject in need thereof pharmaceutical composition according to claim 8.

* * * * *

UNITED STATES PATENT AND TRADEMARK OFFICE
CERTIFICATE OF CORRECTION

PATENT NO. : 10,093,644 B2
APPLICATION NO. : 15/539199
DATED : October 9, 2018
INVENTOR(S) : Guo et al.

Page 1 of 1

It is certified that error appears in the above-identified patent and that said Letters Patent is hereby corrected as shown below:

In the Claims

In Column 22, Line 11, in Claim 7, delete "from;" and insert --from-- therefor

In Column 22, Line 57, in Claim 10, after "thereof", insert --the--

Signed and Sealed this
Thirtieth Day of July, 2019

Andrei Iancu
*Director of the United States Patent and Trademark Office*